US009683029B2

(12) United States Patent
Kim et al.

(10) Patent No.: US 9,683,029 B2
(45) Date of Patent: Jun. 20, 2017

(54) ANTIBODY COMPOSITION FOR PREVENTION OR TREATMENT OF MUTANT HEPATITIS B VIRUS INFECTION

(71) Applicant: Green Cross Corporation, Gyeonggi-do (KR)

(72) Inventors: Se-Ho Kim, Gyeonggi-do (KR); Kwang-Won Hong, Gyeonggi-do (KR); Wong-Won Shin, Gyeonggi-do (KR); Ki Hwan Chang, Gyeonggi-do (KR)

(73) Assignee: GREEN CROSS CORPORATION, Gyeonggi-Do (KR)

( * ) Notice: Subject to any disclaimer, the term of this patent is extended or adjusted under 35 U.S.C. 154(b) by 0 days.

(21) Appl. No.: 14/412,138

(22) PCT Filed: Jul. 8, 2013

(86) PCT No.: PCT/KR2013/006025
§ 371 (c)(1),
(2) Date: Dec. 30, 2014

(87) PCT Pub. No.: WO2014/010890
PCT Pub. Date: Jan. 16, 2014

(65) Prior Publication Data
US 2015/0166637 A1    Jun. 18, 2015

(30) Foreign Application Priority Data

Jul. 10, 2012    (KR) .................. 10-2012-0075063

(51) Int. Cl.
| | |
|---|---|
| A61K 38/21 | (2006.01) |
| C07K 16/40 | (2006.01) |
| C07K 16/08 | (2006.01) |
| A61K 39/42 | (2006.01) |
| A61K 45/06 | (2006.01) |
| A61K 39/00 | (2006.01) |

(52) U.S. Cl.
CPC ............ C07K 16/082 (2013.01); A61K 38/21 (2013.01); A61K 39/42 (2013.01); A61K 45/06 (2013.01); C07K 16/40 (2013.01); *A61K 2039/505* (2013.01); *C07K 2317/34* (2013.01); *C07K 2317/76* (2013.01)

(58) Field of Classification Search
CPC .. A61K 39/12; C07K 14/005; C07K 2319/00; C07K 16/082; C12N 2740/16043; C12N 2740/16222; C12N 2740/16122
See application file for complete search history.

(56) References Cited

U.S. PATENT DOCUMENTS

| | | | |
|---|---|---|---|
| 2004/0219154 A1 | 11/2004 | Jolivet-Reynaud et al. | |
| 2009/0081667 A1 | 3/2009 | Bartholomeusz et al. | |
| 2010/0260712 A1 | 10/2010 | Kim et al. | |

FOREIGN PATENT DOCUMENTS

| | | |
|---|---|---|
| CN | 1600856 A | 3/2005 |
| JP | 11-178591 A | 7/1999 |
| JP | 2005-516617 A | 6/2005 |
| KR | 10-2003-0061568 A | 7/2003 |
| WO | 03066841 A1 | 8/2003 |
| WO | 03087351 A1 | 10/2003 |
| WO | 2006112838 A1 | 10/2006 |
| WO | 2009069916 A1 | 6/2009 |
| WO | WO2009069917 * | 6/2009 |
| WO | 2011078456 A1 | 6/2011 |

OTHER PUBLICATIONS

Tan, Y., et al., "The naturally occurring YMDD mutation among patients chronically infected HBV and untreated with lamivudine: a systematic review and meta-analysis", "PLoS One", Mar. 27, 2012, pp. 1-9, vol. 7, No. 3.
Amini-Bavil-Olyaee, S., et al., "Differential Impact of Immune Escape Mutations G145R and P120T on the Replication of Lamivudine-Resistant Hepatitis B Virus e Antigen-Positive and -Negative Strains", "Journal of Virology", Jan. 2010, pp. 1026-1033, vol. 84, No. 2.
Fischer, K., et al., "Lamivudine resistance in hepatitis B: mechanisms and clinical implications", "Drug Resistance Updates", 2001, pp. 118-128, vol. 4.
Choi, Y., et al., "Hepatitis B Virus from South Korea, complete genome", "GenBank Accession No. DQ683578.1", Jun. 12, 2006, pp. 1-3.
Shin, D., et al., "Efficient inhibition of hepatitis B virus replication by small interfering RNAs targeted to the viral X gene in mice", "Virus Research", Jan. 26, 2006, pp. 146-153, vol. 119.

* cited by examiner

*Primary Examiner* — Bao Li
(74) *Attorney, Agent, or Firm* — Hultquist, PLLC; Steven J. Hultquist

(57) ABSTRACT

The present invention provides an antibody that binds to the surface antigen (HBsAg) of hepatitis B virus (HBV) to neutralize the hepatitis B virus. The surface antigen-binding site of the antibody was found to play a very important role in viral replication, and when a mutation in the site occurs, viral replication is significantly inhibited, and thus at least HBV virus cannot cause a mutation in the site.
In the present invention, it was confirmed by the use of patient-derived virus that the antibody of the present invention binds to either YMDD mutant hepatitis B virus, produced by conventional viral replication inhibitors, or G145R HBsAg mutants to which plasma-derived HBIG (hepatitis B immunoglobulin) does not bind.
In addition, the in vivo effect of the antibody of the present invention was examined using chimpanzees which are unique animal models for hepatitis B virus. As a result, it was found that the antibody has the effect of neutralizing even wild-type hepatitis B virus in the in vivo model. Thus, it can be seen that the antibody of the present invention has the ability to bind not only to wild-type hepatitis B virus, but also mutant hepatitis B viruses having a polymerase YMDD mutant and a surface antigen G145R mutation, as well as various mutant viruses derived from patients.
Thus, the antibody of the present invention can be effectively used for the prevention or treatment of infections with not only wild-type hepatitis B virus, but also mutant hepatitis B viruses.

15 Claims, 3 Drawing Sheets

ANTIBODY COMPOSITION FOR PREVENTION OR TREATMENT OF MUTANT HEPATITIS B VIRUS INFECTION

CROSS-REFERENCE TO RELATED APPLICATIONS

This application is a U.S. national phase under the provisions of 35 U.S.C. §371 of International Patent Application No. PCT/KR13/06025 filed Jul. 8, 2013, which in turn claims priority of Korean Patent Application No. 10-2012-0075063 filed Jul. 10, 2012. The disclosures of such international patent application and Korean priority patent application are hereby incorporated herein by reference in their respective entireties, for all purposes.

TECHNICAL FIELD

The present invention relates to a composition for preventing or treating a disease caused by mutant hepatitis B virus, which contains, as an active ingredient, a neutralizing antibody against mutant human hepatitis B virus (HBV) to which a conventional viral replication inhibitor (e.g., lamivudine or adefovir dipivoxil) or a plasma-derived HBIG (hepatitis B immunoglobulin) does not work or bind.

BACKGROUND ART

Hepatitis B virus (HBV) is a virus with a DNA genome, which belongs to the Hepadnaviridae family and causes acute and chronic hepatitis. Hepatitis B virus (HBV) is classified into eight genotypes having a difference of about 8% or more in the gene nucleotide sequence, or it is classified into four serotypes adw, adr, ayw and ayr) based on the two antigenic determinants (d/y and w/r) of hepatitis B surface antigen (HBsAg). About 3.5 hundred million people worldwide have chronic hepatitis B virus (HBV) infection, and particularly, in Korea and China, people with chronic hepatitis B virus infection reach about 5-8%, and hepatitis B virus (HBV) infection is the major cause of liver disease and liver cancer. Currently developed vaccines can be somewhat effective in the prevention of hepatitis B virus infection, but a significant number of patients with chronic infection with hepatitis B virus still exist. Chronic infection with hepatitis B virus (HBV) causes hepatitis, cirrhosis and liver cancer, and the incidence of liver cancer is about 300 times higher in people with chronic hepatitis B virus than in non-infected people. According to the WHO report, about 80% of liver cancer is caused by chronic hepatitis B.

Currently known therapeutic agents for hepatitis B include the nucleoside analogues including lamivudine and adefovir dipivoxil, which inhibit the DNA replication of hepatitis B virus (HBV) by inhibiting the reverse transcriptase of hepatitis B virus polymerase (HBV polymerase). However, when these drugs are administered for 3 years, drug-resistant virus occurs in about 75% of the patients to reduce the therapeutic effect of the drug. Due to this problem, it is impossible treat hepatitis B infection using the viral replication inhibitors alone. For this reason, it was attempted to use these inhibitors in combination with interferon agents, but these inhibitors are not currently used due to serious side effects.

For a similar purpose, a hepatitis B immune globulin (HBIG) preparation comprising a hepatitis B virus (HBV) antibody isolated from blood having a high antibody titer was considered. However, because the antibody of the HBIG preparation is isolated and purified from plasma, there are problems, including difficulty in obtaining plasma, the possibility of viral infection, low activity, high costs and the like.

In recent years, there have been reports of mutant viruses capable of avoiding such antibodies, for example, a mutant having a glycine-to-arginine substitution at position 145 of the surface protein of hepatitis B virus (HBV). In addition, various mutants capable of avoiding the antibodies have appeared. For this reason, it is difficult for the conventional hepatitis B virus therapeutic agents to show satisfactory therapeutic effects.

Thus, there is an urgent need to develop an antibody for treating hepatitis B virus (HBV), which binds specifically to a hepatitis B virus (HBV) epitope in which no mutation occurs, so that the therapeutic effect of the antibody is not reduced by the mutation.

DISCLOSURE OF INVENTION

It is an object of the present invention to provide a composition for preventing or treating a disease caused by infection with a mutant virus having resistance to a conventional therapeutic agent which has been used for the prevention or treatment of hepatitis B virus (hereinafter, referred to as "HBV").

To achieve the above object, the present invention provides an antibody composition for preventing or treating an infection with a HBV having a G145R mutation of HBV surface antigen (HBsAg) or an YMDD (tyrosine-methionine-aspartate-aspartate) mutation of HBV DNA polymerase (SEQ ID NO: 13), the composition comprising an antibody comprising:

a heavy-chain variable region having any one amino acid sequence selected from among SEQ ID NO: 1 to SEQ ID NO: 5; and a light-chain variable region having any one amino acid sequence selected from among SEQ ID NO: 6 to SEQ ID NO: 10.

Other features and embodiments of the present invention will be more apparent from the following detailed descriptions and the appended claims.

BRIEF DESCRIPTION OF THE DRAWINGS

In FIG. 2(a), 1: 0.1 μg of the antibody of the present invention, 2: 0.5 μg of the antibody of the present invention, 3: 1 μg of the antibody of the present invention, 4: 5 μg of the antibody of the present invention, and 5: PBS buffer.

In FIG. 2(c), 1: PBS, 2: treated with 1 μg of anti-tetanus toxoid human antibody (TT-F9), 3: treated with 1 μg of Hepabig, 4: treated with 1 μg of anti-hepatitis B virus surface antigen humanized antibody (HuS 10), and 5: treated with 1 μg of the antibody of the present invention.

FIG. 3(a) is a photograph showing that the antibody of the present invention was strongly bound to HBV-infected human liver tissue, and FIG. 3(b) is a photograph showing isotype negative control antibody was not bound to the same tissue.

BEST NODE FOR CARRYING OUT THE INVENTION

Figure 1:
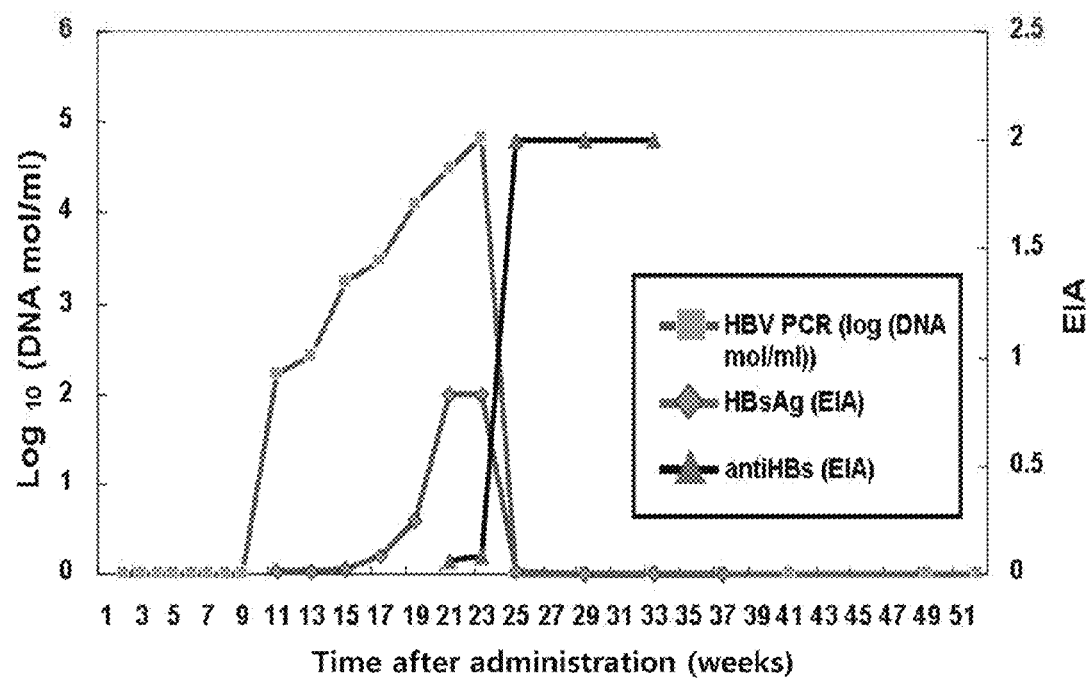
FIG. 1 is a graphic diagram showing the HBV-neutralizing activity of the antibody of the present invention in chimpanzees.

Hereinafter, the present invention will be described in further detail.

The present invention is directed to an antibody composition for preventing or treating an infection with a HBV having a G145R mutation of HBV surface antigen (HBsAg) or a YMDD (tyrosine-methionine-aspartate-aspartate) mutation of HBV DNA polymerase, the composition comprising an antibody comprising:

a heavy-chain variable region having any one amino acid sequence selected from among SEQ ID NO: 1 to SEQ ID NO: 5; and a light-chain variable region having any one amino acid sequence selected from among SEQ ID NO: 6 to SEQ ID NO: 10.

The antibody according to the present invention may be an antibody against a HBV surface antigen (HBsAg) having a G145R mutation or a DNA polymerase YMDD motif mutation, produced from the cell line HBAb-49 (KCLRF-BP-00054). The G145R mutation is a glycine-to-arginine substitution at position 145 of HBV surface protein, to which plasma-derived HBIG does not bind, and the YMDD motif is located in the C end region of the DNA polymerase gene of hepatitis B virus and has a methionine (M)-to-valine (V) or isoleucine (I) substitution at position 552 of the amino acid sequence.

The antibody composition is used for the prevention or treatment of infection with mutant virus resistant to the HBV therapeutic agent lamivudine or adefovir dipivoxil.

In addition, the antibody composition may further comprise an antiviral agent. The antiviral agent is preferably one or more selected from among interferon, anti-HBV monoclonal antibodies, anti-HBV polyclonal antibodies, nucleoside analogues, DNA polymerase inhibitors, and siRNA preparations, but is not limited thereto.

The antibody composition preferably contains the antibody at a concentration of 0.1-50 mg/ml. The present invention also provides a pharmaceutical formulation containing the antibody composition as an active ingredient. The pharmaceutical formulation is preferably administered to mammals including human at a dose of 0.001-10 mg/kg (bodyweight).

The pharmaceutical composition may be prepared into a pharmaceutical formulation in accordance with any conventional method. In preparation of the formulation, the antibody is preferably admixed or diluted with a carrier, or enclosed within a carrier. When the carrier is used as a diluent, it may be a solid, semi-solid or liquid material acting as a vehicle, excipient or medium for the active ingredient.

Thus, the formulations may be in the form of a tablet, pill, powder, sachet, elixir, suspension, emulsion, solution, syrup, aerosol, soft and hard gelatin capsule, sterile injectable solution, sterile packaged powder and the like.

Examples of suitable carriers, excipients, and diluents include lactose, dextrose, sucrose, sorbitol, mannitol, starches, gum acacia, alginates, gelatin, calcium phosphate, calcium silicate, cellulose, methyl cellulose, microcrystalline cellulose, polyvinylpyrrolidone, water, methylhydroxybenzoates, propylhydroxybenzoates, talc, magnesium stearate and mineral oil. The formulations may additionally include fillers, anti-agglutinating agents, lubricating agents, wetting agents, flavoring agents, emulsifiers, preservatives and the like. The compositions of the invention may be formulated according to any method well known in the art so as to provide quick, sustained or delayed release of the active ingredient after their administration to a mammal.

In an experiment performed to demonstrate the HBV neutralizing activity of the antibody of the present invention using chimpanzees, it was shown that the chimpanzees were not infected with HBV for one year after administration of a mixture of HBV and the antibody. In chimpanzees used in a control group, it was shown that the HBV virus particle and surface antigen were produced and an antibody against the HBV surface antigen was produced during the recovery stage (see FIG. 1).

Figure 2:
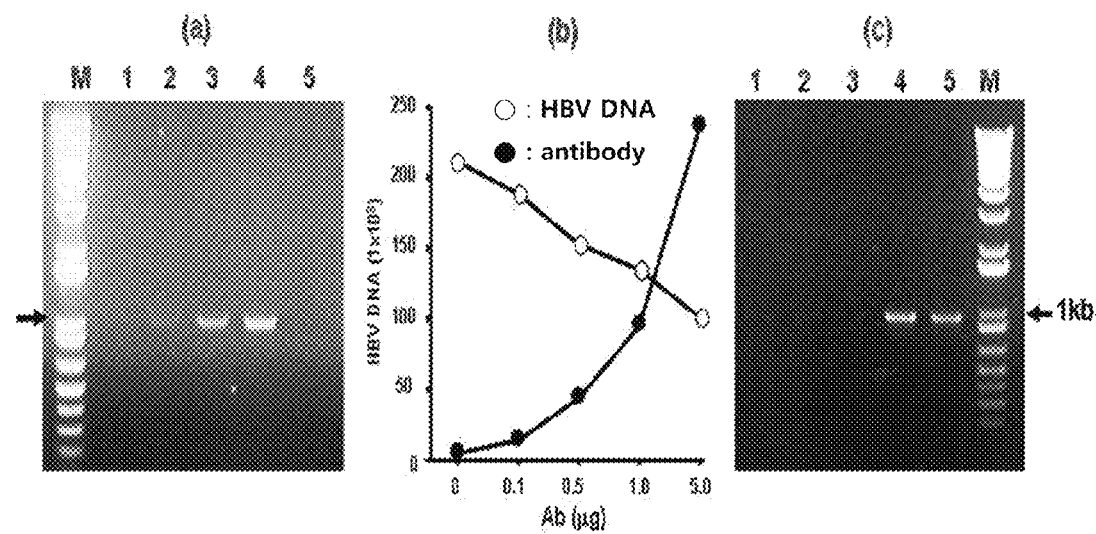
FIG. 2 depicts photographs (see FIGS. 2a and 2c) and a graphic diagram (see FIG. 2b), which show the results of immunoprecipitation assay performed to examine whether the antibody of the present invention binds to the HBV of the blood of hepatitis B patients.
Figure 3:
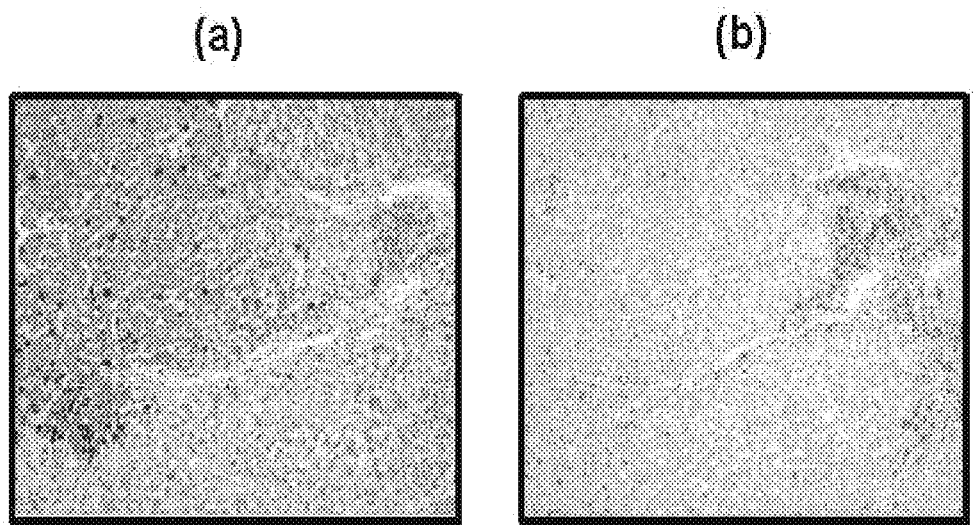
FIG. 3 is a set of photographs showing the results of an immunohistochemical staining assay performed to examine whether antibodies bind to human liver tissue infected with HBV. Specifically.

In addition, it was shown by an immunoprecipitation assay that the antibody of the present invention had an excellent ability to bind to the HBV of patient blood (see FIG. 2). In addition, it was shown by an immunohistochemical staining assay that the antibody of the present invention did strongly bind to HBV-infected human liver tissue (see FIG. 3).

The antibody according to the present invention may have the ability to bind to and neutralize the HBsAg of antibody-resistant and antibody-escapable HBV which cannot be inhibited by a conventional viral replication inhibitor (lamivudine or adefovir dipivoxil) or plasma-derived HBIG. In an example of the present invention, the binding ability of the antibody was examined by an enzyme-linked immunosorbent assay (ELISA) using patient's blood containing YMDD mutant virus having an YMDD mutation on the reverse transcriptase of hepatitis B virus polymerase, which has resistance to viral replication inhibitors. As a result, it was shown that the antibody strongly bind to all the YMDD mutant viruses (see Table 5 and Table 6).

The biggest characteristic of the antibody of the present invention is its ability to bind to and neutralize a mutant having a glycine-to-arginine substitution at position 145 of HBV surface protein, which cannot be neutralized by plasma-derived HBIG. To verify this ability, mutant virus was produced using a hydrodynamic mouse model, and whether the antibody has the ability to neutralize the produced mutant virus was examined. As a result, it was shown that HBsAg and HBV in the blood of the mouse model were all removed (see FIG. 5).

It was shown that the antibody of the present invention did bind to hepatitis B viruses (HBVs) of patients, which recurred after liver transplantation, and that the HBV viruses were all mutants having a glycine-to-arginine substitution at position 145 of HBV surface protein (see Table 8).

The above-described results suggest that the antibody of the present invention and a composition comprising the same can be effectively used for the prevention or treatment of infection with mutant HBV virus having resistance to conventional therapeutic agents. Particularly, it can be seen that the antibody and the composition can be very effectively used for the prevention or treatment of infection with G145R mutant HBV or YMDD motif mutant HBV.

EXAMPLES

Hereinafter, the present invention will be described in further detail with reference to examples. It will be obvious to a person having ordinary skill in the art that these examples are illustrative purposes only and are not to be construed to limit the scope of the present invention.

Example 1

Experiment on HBV-Neutralizing Ability in Chimpanzees

In order to examine whether the antibody of the present invention has the ability to neutralize HBV in vivo, the following experiment was performed.

HBV 100 $CID_{50}$ (50% chimpanzee infectious doses) obtained from the Hepatitis Research Foundation (USA) was placed in three tubes. The antibody of the present invention comprising a heavy-chain variable region having amino acid sequence of SEQ ID NO: 2 and a light-chain variable region having amino acid sequence of SEQ ID NO: 7 was added to two of the three tubes in amounts of 0.1 mg and 10 mg, respectively, and no antibody was added to the remaining one tube. The mixture in each of the tubes was adjusted to a volume of 3 ml with PBS (phosphate buffered saline) buffer, after which the mixture was allowed to react at 37° C. for 1 hour, and then at 4° C. overnight, followed by freezing with liquid nitrogen, thereby preparing test materials.

For an animal experiment, the test materials were administered intravenously to three chimpanzees, respectively, which have never been infected with HBV (see Table 1).

TABLE 1

Dose of antibody administered to each chimpanzee

|  | Sex | Age (years) | Weight (kg) | Dose of antibody |
|---|---|---|---|---|
| Controls | Chimpanzee 1 Male | 4 | 12.2 | — |
| Test group 1 | Chimpanzee 2 Male | 4 | 11.6 | 0.1 mg |
| Test group 2 | Chimpanzee 3 Female | 4 | 10.8 | 10 mg |

At 1-week intervals during a period ranging from 1 week after antibody administration to 8 weeks after antibody administration and at 2-week intervals after antibody administration, blood was collected from the chimpanzees to measure HBV infection-related indices, including HBV DNA, HBsAg (HBV surface antigen), anti-HBs (HBV surface antigen antibody), anti-HBc (HBV core antibody), ALT, AST and the like. In addition, the in vivo safety of the antibody was analyzed by blood and urine examinations.

In addition, the changes in the HBV DNA, HBsAg and anti-HBs of chimpanzee were measured, and the results of the measurement are graphically shown in FIG. 1.

As shown in Tables 2, 3 and 4, HBV infection was observed in chimpanzee 1 as the control, whereas no HBV infection was observed in chimpanzees 2 and 3, administered with antibody together with HBV, throughout the experimental period. Such results revealed that the antibody of the present invention has an excellent ability to neutralize HBV. In addition, no special abnormal findings were observed in liver function examination, various hematological examinations, urine examination and the like, suggesting that the antibody is safe in vivo.

TABLE 2

Measurement of HBV infection indices (chimpanzee 1)

| Time from administration | ALT (sf units) | AST (sf units) | HBV PCR $Log_{10}$ (DNA mol/ml) | HBsAG (EIA) | Anti-HBs (EIA) | Anti-HBc (EIA) |
|---|---|---|---|---|---|---|
| Before 1 week | 6 | 11 | N | | | |
| Admin. day | 5 | 10 | N | | | |
| After 1 week | 15 | 13 | N | | | |
| After 2 weeks | 6 | 16 | N | | | |
| After 3 weeks | 8 | 22 | N | | | |
| After 4 weeks | 2 | 6 | N | | | |
| After 5 weeks | 6 | 11 | N | | | |
| After 6 weeks | 5 | 12 | N | | | |
| After 7 weeks | 6 | 20 | N | | | |
| After 8 weeks | 7 | 18 | N | | | |
| After 10 weeks | 8 | 18 | 2.21 | .015 (−) | | |
| After 12 weeks | 10 | 23 | 2.43 | .023 (−) | | |
| After 14 weeks | 13 | 25 | 3.24 | .064 (−) | | |
| After 16 weeks | 12 | 18 | 3.47 | .209 (+) | | |
| After 18 weeks | 8 | 20 | 4.10 | .600 (+) | | 1.004 (−) |
| After 20 weeks | 8 | 13 | 4.50 | >2.000 (+) | | 1.264 (−) |
| After 22 weeks | 10 | 12 | 4.82 | >2.000 (+) | .056 (−) | 1.038 (−) |
| After 24 weeks | 15 | 18 | N | 0.03 (−) | .085 (−) | .0129 (+) |
| After 28 weeks | 23 | 22 | N | N | >2.000 (+) | 0.156 (+) |
| After 32 weeks | 19 | 18 | N | N | >2.000 (+) | 0.119 (+) |
| After 36 weeks | 21 | 19 | N | N | >2.000 (+) | 0.061 (+) |
| After 40 weeks | 7 | 23 | N | | | |
| After 44 weeks | 25, 24 | 19 | N | | | |
| After 48 weeks | 19 | 16 | N | | | |
| After 51 weeks | 28, 29 | 23 | N | | | |

TABLE 3

Measurement of HBV infection indices (chimpanzee 2)

| Time from administration | ALT (sf units) | AST (sf units) | HBV PCR $Log_{10}$ (DNA mol/ml) | Anti-HBs (EIA) | Anti-HBc (EIA |
|---|---|---|---|---|---|
| Before 1 week | 26 | 22 | N | | |
| Admin. day | 9 | 26, 25 | N | | |
| After 1 week | 10 | 23 | N | | |
| After 2 weeks | 6 | 24 | N | | |
| After 3 weeks | 9 | 25 | N | | |
| After 4 weeks | 4 | 18 | N | (−) | |
| After 5 weeks | 9 | 37, 37 | N | (−) | |
| After 6 weeks | 5 | 25 | N | (−) | |
| After 7 weeks | 5 | 9 | N | (−) | |
| After 8 weeks | 5 | 13 | N | (−) | |
| After 10 weeks | 8 | 17 | N | | |
| After 12 weeks | 14 | 21 | N | | |
| After 14 weeks | 17 | 23 | N | | |
| After 16 weeks | 15 | 19 | N | | |
| After 18 weeks | 22 | 16 | N | | |
| After 20 weeks | 20 | 16 | N | | |
| After 22 weeks | 13 | 19 | N | | |
| After 24 weeks | 24 | 22 | N | | |
| After 28 weeks | 28, 28 | 25 | N | | |
| After 32 weeks | 24 | 26 | N | | |
| After 36 weeks | 23 | 25 | N | | |
| After 40 weeks | 11 | 20 | N | | |
| After 44 weeks | 27, 27 | 17 | N | | |
| After 48 weeks | 18 | 13 | N | N | |
| After 51 weeks | 30, 29 | 24 | N | | N |

TABLE 4

Measurement of HBV infection indices (chimpanzee 3)

| Time from administration | ALT (sf units) | AST (sf units) | HBV PCR Log$_{10}$ (DNA mol/ml) | HBsAG (EIA) | Anti-HBs (EIA) | Anti-HBc (EIA) |
|---|---|---|---|---|---|---|
| Before 1 week | 5 | 18 | N | | | |
| Admin. day | 11 | 22 | N | | | |
| After 1 week | 7 | 18 | N | | | |
| After 2 weeks | 5 | 20 | N | | | |
| After 3 weeks | 13 | 31, 31 | N | | | |
| After 4 weeks | 9 | 19 | N | (−) | (−) | |
| After 5 weeks | 8 | 23 | N | (−) | (−) | |
| After 6 weeks | 14 | 26 | N | (−) | (−) | |
| After 7 weeks | 7 | 15 | N | (−) | (−) | |
| After 8 weeks | 10 | 19 | N | (−) | (−) | |
| After 10 weeks | 20 | 16 | N | | | |
| After 12 weeks | 13 | 19 | N | | | |
| After 14 weeks | 16 | 21 | N | | | |
| After 16 weeks | 16 | 24 | 2.24*, N, N | | | |
| After 18 weeks | 21 | 24 | N | | | |
| After 20 weeks | 14 | 22 | N | | | |
| After 22 weeks | 16 | 19 | N | | | |
| After 24 weeks | 21 | 17 | N | | | |
| After 28 weeks | 18 | 21 | N | | | |
| After 32 weeks | 23 | 16 | N | | | |
| After 36 weeks | 22 | 17 | N | | | |
| After 40 weeks | 16 | 23 | N | | | |
| After 44 weeks | 24, 25 | 15 | 2.24*, N, N | | | |
| After 48 weeks | 20 | 19 | N | N | | |
| After 51 weeks | 28, 31 | 22 | N | | | N |

(*borderline (+))

Example 2

Examination of HBV-Binding Ability of Antibody by Immunoprecipitation

Whether the antibody of the present invention comprising heavy-chain variable region having amino acid sequence of SEQ ID NO: 2 and a light-chain variable region having amino acid sequence of SEQ ID NO: 7 binds to HBV in hepatitis B patient blood (provided from Ajou University School of Medicine) was examined by immunoprecipitation (see FIG. 2).

(1) Preparation of Hepatitis B Patient Blood 1,000 μl of a 10-fold dilution of hepatitis B patient blood in 0.2% BSA/PBS buffer was allowed to react with a goat anti-human IgG (Fc specific)-agarose conjugate (Research Diagnostics Inc., Flanders, N.J.) to remove immunoglobulin from the blood.

(2) Binding Reaction Between Antibody and Goat Anti-Human IgG-Agarose Conjugate

10 μl of the antibody of the present invention (0.1, 0.5, 1 and 5 μg), PBS solution and 50 μl of a goat anti-human IgG-agarose conjugate (Research Diagnostics) were mixed with each other and allowed to react with stirring at room temperature for 1 hour, and then 10 mg of human immunoglobulin (I.V.-Globulin-S, Green Cross) was added thereto and allowed to react with stirring at room temperature for 1 hour so as to block the binding portion of the goat anti-human IgG-agarose conjugate. For comparison, 1 μg of each of blood HBV antibody (Hepabig), TT-F9 (anti-tetanus toxoid human antibody) and HuS 10 (anti-hepatitis B virus surface antigen humanized antibody) was used in the same manner as above.

(3) Binding Reaction Between Antibody-Bound Goat Anti-Human IgG-Agarose Conjugate and Patient Blood 200 μl of the blood prepared in Example 2-(1) was mixed with the antibody-bound goat anti-human IgG-agarose conjugate prepared in Example 2-(2), and the mixture was stirred at room temperature for 1 hour to allow the antibody to react with the HBV of the patient blood.

(4) Examination of Precipitation of HBV

The reaction solution of Example 2-(3) was centrifuged, and the supernatant was collected and HBV in the supernatant was measured using a Cobas Amplicor HBV Monitor Test (v2.0; Roche Diagnostics, Basel, Switzerland).

The agarose remaining after centrifugation was washed 10 times with 0.2% BSA/PBS buffer, and then added to 100 μl of the same buffer, and 5 μl of 10% SDS, 2 μl of 50 mM EDTA and 200 μg of protease K (Sigma-Aldrich) were added thereto and allowed to react at 55° C. for 30 minutes. Then, the supernatant was collected and DNA was isolated therefrom using a QIAquick PCR purification kit (Qiagen, Hilden, Germany), after which HBV-specific DNA was amplified by PCR using a LiquiMix GM PCR premix (Neurotics, Korea), primer M3 (SEQ ID NO: 11) and primer POL8 (SEQ ID NO: 12). Herein, the PCR was performed under the following conditions: initial denaturation at 55° C. for 5 minutes, and then 35 cycles of 1 min at 95° C., 1 min at 55° C. and 1 min at 72° C., followed by final extension at 72° C. for 10 min. The amplified DNA was analyzed on 1.0% agarose gel. As controls, HBV humanized antibody and tetanus toxoid human antibody (Green Cross, Korea) were used. The results of the analysis are shown in FIG. 2.

As shown in FIGS. 2(a) and 2(b), the amount of precipitation of HBV increased as the amount of antibody used in the immunoprecipitation reaction increased, and the amount of HBV in the supernatant after the immunoprecipitation reaction increased as the amount of the antibody decreased. Also, the amount of precipitation of HBV increased as the amount of the antibody increased. In addition, as shown in FIG. 2(c), when the same amount of the antibody was used, the HBV antibody (Hepabig) purified from blood did not precipitate HBV due to its low ability to bind to HBV, whereas the antibody of the present invention did precipitate HBV due to its high ability to bind to HBV.

Example 3

Examination of HBV-Binding Ability of Antibody by Immnunohistochemistry

Whether the antibody of the present invention comprising heavy-chain variable region having amino acid sequence of SEQ ID NO: 2 and a light-chain variable region having amino acid sequence of SEQ ID NO: 7 binds to HBV-infected tissue was examined by immnunohistochemistry.

A frozen slide having HBV-infected human liver tissue (Spring Bioscience, Fremont, Calif., USA, Catalog No. STS-025) was fixed with acetone and allowed to react with a dilution of hydrogen peroxide in methanol. Then, the tissue slide was allowed to react with normal rabbit serum, followed by sequential reactions with avidin and biotin. Then, the tissue slide was allowed to react with each of the antibody of the present invention and an isotype human immunoglobulin (IgG1 isotype negative control antibody; Sigma-Aldrich), which were biotinylated using an immuno-probe biotinylation kit (Sigma-Aldrich), and the tissue slide was allowed to react with StreptABComplex/HRP (Dako, Holland). Each of the reaction products was stained with 3,3'-diaminobenzidine tetrahydrochloride (DAB) and counterstained with haematoxylin, and the results of the staining are shown in FIGS. 3(a) and 3(b).

As can be seen in FIGS. 3(a) and 3(b), the isotype negative control antibody (see FIG. 3(b)) did not bind to the HBV-infected human liver tissue, whereas the antibody of the present invention (see FIG. 3(a)) did strongly bind to the HBV-infected human liver tissue.

Example 4

Examination of the Ability to Bind to HBV Replication Inhibitor-Resistant Mutant In order to examine whether the antibody of the present invention comprising heavy-chain variable region having amino acid sequence of SEQ ID NO: 2 and a light-chain variable region having amino acid sequence of SEQ ID NO: 7 binds, patient blood samples (provided from St. Mary's Hospital, Catholic University) were allowed to react in a 96-well plate coated with the antibody of the present invention, and detection was performed using a sheep anti-HBsAg/peroxidase conjugate in a Genedia HBsAg ELISA 3.0 kit (Green Cross MS, Korea). As a result, as shown in Table 5 below, the antibody of the present invention did strongly bind to the HBsAg of all YMDD mutant viruses. Thus, as can be seen in Table 5, the antibody of the present invention can bind to YMDD mutant virus in the blood of chronic hepatitis B (CHB) patients.

TABLE 5

Results of enzyme-linked immunosorbent assay (ELISA) for the ability of the antibody of the present invention to bind to YMDD mutant virus

| Sample | A450 |
| --- | --- |
| (−) Control | 0.063 |
|  | 0.09 |
|  | 0.058 |
| (+) Control | 0.488 |
|  | 0.524 |
| YMDD #1 | 1.16 |
| YMDD #3 | 0.957 |
| YMDD #4 | 1.019 |
| YMDD #5 | 0.356 |
| YMDD #6 | 1.043 |
| YMDD #7 | 1.104 |
| YMDD #8 | 1.143 |
| YMDD #9 | 0.834 |
| YMDD #10 | 1.134 |
| YMDD #11 | 0.786 |
| YMDD #12 | 0.876 |
| YMDD #13 | 1.066 |
| YMDD #14 | 0.815 |
| YMW(+) | 0.747 |
| CSY(+) | 1.023 |
| SYW(−) | 0.073 |
| Q101K, I126N, G145A | 0.857 |
| BSA(−) | 0.251 |
|  | 0.263 |

Example 5

Examination of the Ability to Bind to Various HBsAg Mutants Derived from Chronic Hepatitis B, Liver Cirrhosis and Hepatocellular Carcinoma Virus surface antigen (HBsAg) mutants derived from 100 chronic hepatitis B (CHB) patients, 100 liver cirrhosis (LC) patients and 100 hepatocellular carcinoma (HCC) patients were analyzed to examine whether the antibody of the present invention comprising heavy-chain variable region having amino acid sequence of SEQ ID NO: 2 and a light-chain variable region having amino acid sequence of SEQ ID NO: 7 bind to all the mutant viruses. Patient blood samples (provided from St. Mary's Hospital, Catholic University) were allowed to react in a 96-well plate coated with the antibody of the present invention, and detection was performed using a sheep anti-HBsAg/peroxidase conjugate in a Genedia HBsAg ELISA 3.0 kit (Green Cross MS, Korea). As a result, as shown in Table 6 below, the antibody of the present invention did strongly bind to all the HBsAg mutants derived from the patients.

TABLE 6

Results of measurement of binding of the antibody of the present invention to typical surface antigen mutant viruses

| Patient number | ELISA | NDA titer | S mutation (amino acid 124-147) |
| --- | --- | --- | --- |
| CH 15 | 3.059 | $3.864*10^3$ | L110M, T113S, S114T, L126T, G130D, T131D, S143T, R160K |
| CH 32 | 2.949 | $10^8$ | P142T |
| CH 33 | 2.833 | $10^8$ | L126S |
| CH 34 | 1.37 | $56646*10^3$ | Y100S, L126S, T131N, M133T |
| CH 62 | 3.085 | $10^8$ | T131L, R160K |
| CH 75 | 2.933 | $10^8$ | L126S, T131N, M133T |
| LC 32 | 2.726 | <2.5 pcr | P127R, Q129K, T131A, M133L, T140S, K141R, P142S, C147Y, A159W |
| LC 53 | 3.497 | <2.5 pcr | L126T |
| LC 59 | 3.633 | <2.5 pcr | T131P |
| LC 98 | 3.553 | $9761*10^3$ | G130N |
| HCC 1 | 3.611 | $11943*10^3$ | Q101K, L126T |
| HCC 11 | 3.358 | $>100000*10^3$ | L126T, G130N, R160K |
| HCC 22 | 3.517 | $270.8*10^3$ | Y100C, L126T |
| HCC 94 | 3.556 | $39687*10^3$ | T123A, S143W |

[CH: (chronic hepatitis, 100 patients); LC: liver cirrhosis, 100 patients); HCC: (hepatocellular carcinoma, 100 patients)]

Example 6

Examination of In Vivo Effect of Antibody in Acute Hepatitis B-Induced Mice

In this Example, C57BL6 mice showing symptoms similar to acute hepatitis B were made by injecting HBV DNA into mice by hydrodynamic injection, and the ability of the antibody of the present invention comprising heavy-chain variable region having amino acid sequence of SEQ ID NO: 2 and a light-chain variable region having amino acid sequence of SEQ ID NO: 7 to neutralize hepatitis B surface antigen (HBsAg) was measured.

Figure 4:
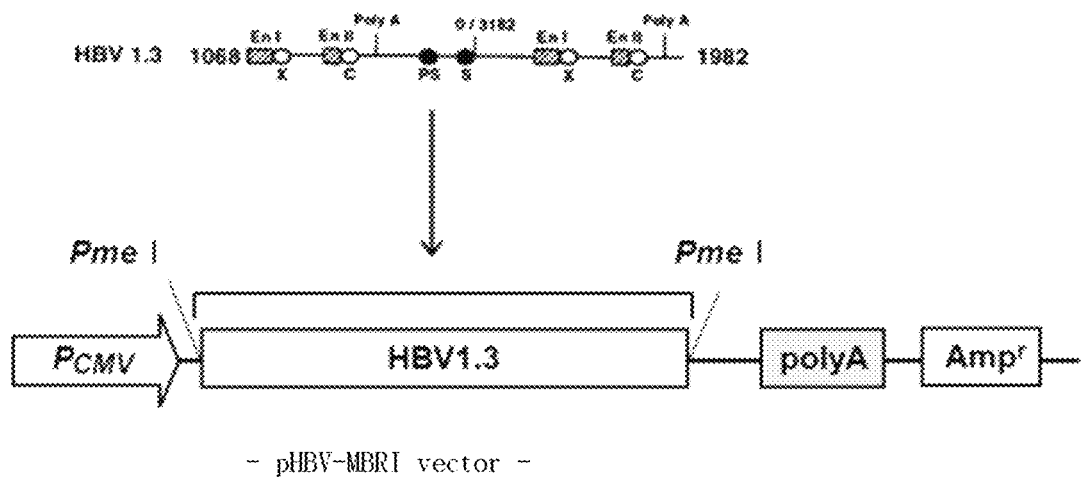
FIG. 4 is a genetic map of hepatitis B virus (HBV). The plasmid pHBV1.3-MBRI was constructed by inserting an 1.3-fold sequence of an HBV (adr subtype) gene (Gene Bank Accession No. DQ683578) (HBV gene from upstream of enhancer I of an HBV genome to downstream of a polyadenylation region) into the PmeI restriction enzyme site of pcDNA3.1 (Invitrogen, USA).

The C57BL6 mice used were twenty 6-week-old female mice (weight: about 20 g; purchased from Charles Liver Laboratory, MA, USA) and divided into 4 groups, each consisting of 5 mice, as shown in Table 7 below. 20 μg of a pHBV-MBRI vector (Shin et al., Virus Research 119, 146-153, 2006; see FIG. 4) obtained by inserting a HBV DNA nucleotide sequence into pcDNA3.1 (Invitrogen, USA) was diluted to a volume corresponding to 9.5% of the mouse weight and was injected into the tail vein of each of the mice at a rate of 0.3 ml/min to induce acute hepatitis B in the mice. After 24 hours, 0.2 ml of the test material shown in Table 7 below was injected into the tail vein of each of the mice. Before injection of the test material (0 hr) and at 24 and 48 hours after injection, blood was collected from the mice, and serum was separated therefrom and diluted 10-fold with goat serum, after which the concentration of HBsAg in the blood was measured using Genedia HBsAg ELISA 3.0 (Green Cross MS, Korea).

TABLE 7

Experimental design for measuring the ability to neutralize hepatitis B surface antigen (HBsAg) in mouse blood

| Group | Number | Test material and path | Dose |
| --- | --- | --- | --- |
| HBsAg (ayw) | 5 | PBS, intravenous injection | 0.2 mL |
| HBsAg (ayw) | 5 | rHBIG 0.1 mg (400 IU), intravenous injection | 0.2 mL |
| G145R | 5 | PBS, intravenous injection | 0.2 mL |
| G145R | 5 | rHBIG 0.1 mg (400 IU), intravenous injection | 0.2 mL |

Figure 5:
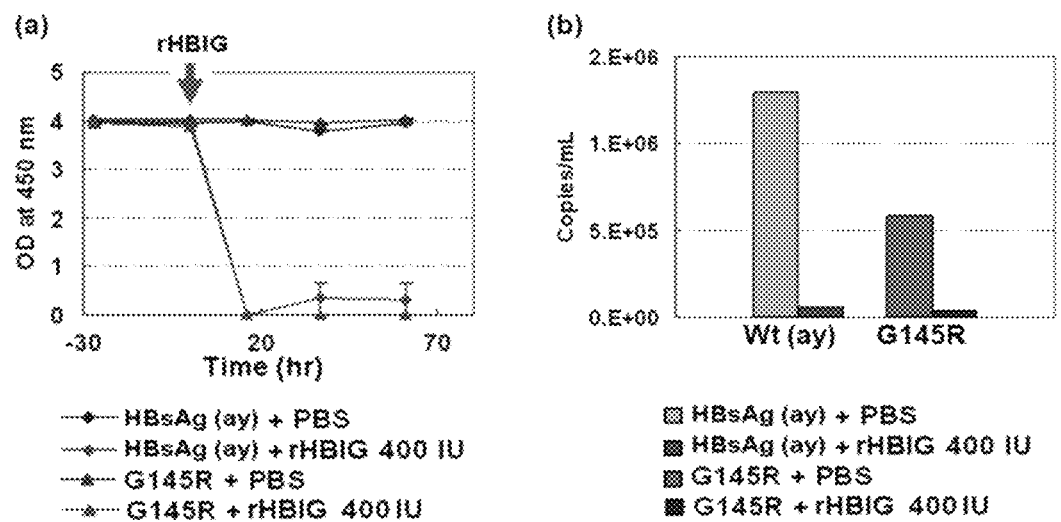
FIG. 5 shows the results of an experiment performed to examine the neutralizing activity of an antibody against G145R mutant virus using a hydrodynamic mouse model and indicates that the surface antigen and viral particles of wild-type HBV and G145R mutant HBV were all removed from mouse blood.

The results of the measurement are shown in FIG. 5. As can be seen in FIG. 5(a), in the control group injected intravenously with PBS among the wild-type virus groups, the blood HBsAg concentration and the HBV DNA replication were maintained at the peak levels up to 48 hours, whereas in the group administered with 0.1 mg of the antibody rHBIG, blood HBsAg and HBV DNA replication were not substantially detected after 24 hours up to 48 hours due to complete neutralization. In addition, as can be seen in FIG. 5(b), in the control group administered intravenously with PBS among the G145R mutant virus groups, the blood HBsAg concentration and the HBV DNA were maintained at the peak levels up to 48 hours, whereas in the group administered with 0.1 mg of the antibody, blood HBsAg and HBV DNA replication were not substantially detected after 24 hours up to 48 hours due to complete neutralization. Thus, the above-described results indicate that the antibody of the present invention comprising heavy-chain variable region having amino acid sequence of SEQ ID NO: 2 and a light-chain variable region having amino acid sequence of SEQ ID NO: 7 has a very excellent neutralization effect against the wild-type and G145R mutant HBV surface antigens. In addition, the number of HBV DNA copies in each of the groups was quantified using real-time PCR, and as a result, viral DNA was detected in both the wild-type and G145R mutant HBVs. This suggests that the antibody of the present invention has a very excellent neutralization effect against both the wild-type and G145R mutant HBVs.

Example 7

Examination of the Ability to Bind to G145R HBsAg Mutants Derived from Patients in which HBV Recurred by G145R Mutants after Liver Transplantation The ability of the antibody of the present invention comprising heavy-chain variable region having amino acid sequence of SEQ ID NO: 2 and a light-chain variable region having amino acid sequence of SEQ ID NO: 7 to bind to G145R HBsAg mutants derived from patients having a HBV which recurred by a G145R mutation in HBsAg was examined. Patient blood samples were allowed to react in a 96-well plate coated with the antibody of the present invention, and detection was performed using a sheep anti-HBsAg/peroxidase conjugate in a Genedia HBsAg ELISA 3.0 kit (Green Cross MS, Korea). As a result, as can be seen in Table 8 below, the antibody did strongly bind to all the G145R HBsAg mutants.

TABLE 8

Results of measurement of binding of the antibody of the present invention to all HBsAg mutants derived from patients

| Sample | Immobilized antibody rHBIG | Mutation |
| --- | --- | --- |
| S** | 2.526 | G145R |
| C** | 2.471 | G145R |
| B** | 3.078 | G145R |
| L** | 2.717 | G145R |
| W** | 2.660 | G145R |
| Negative control | 0.015 | G145R |
| Positive control | 1.048 | G145R |

INDUSTRIAL APPLICABILITY

As described above, the antibody composition of the present invention can be effectively used for the prevention or treatment of infection with mutant viruses having resistance to conventional therapeutic agents. Particularly, it can be very effectively used for the prevention or treatment of infection with G145R mutant HBV or YMDD motif mutant HBV.

Although the present invention has been described in detail with reference to the specific features, it will be apparent to those skilled in the art that this description is only for a preferred embodiment and does not limit the scope of the present invention. Thus, the substantial scope of the present invention will be defined by the appended claims and equivalents thereof.

The invention claimed is:

1. A composition for preventing or treating an infection with a HBV having a G145R mutation of HBV surface antigen (HBsAg) or a YMDD (tyrosine-methionine-aspartate-aspartate) mutation of HBV DNA polymerase (SEQ ID NO: 13), the composition comprising, as an active ingredient, an antibody comprising a heavy-chain variable region ($V_H$) having the amino acid sequence of SEQ ID NO: 2; and a light-chain variable region ($V_L$) having the amino acid sequence of SEQ ID NO: 7.

2. The composition of claim 1, further comprising another antiviral agent.

3. The composition of claim 2, wherein the antiviral agent comprises one or more selected from the group consisting of interferon, anti-HBV monoclonal antibodies, anti-HBV polyclonal antibodies, nucleoside analogues, DNA polymerase inhibitors, and siRNA preparations.

4. The composition of claim 1, wherein the YMDD mutation is a M552V or M552I mutation.

5. The composition of claim 1, wherein the virus is mutant hepatitis B virus (HBV) resistant to lamivudine, adefovir dipivoxil, or HBIG (hepatitis B immunoglobulin).

6. The composition of claim 1, wherein the antibody is contained at a concentration of 0.1-50 mg/ml.

7. A pharmaceutical formulation containing the composition of claim 1 as an active ingredient.

8. The pharmaceutical formulation of claim 7, further comprising carriers, excipients, and/or diluents.

9. The pharmaceutical formulation of claim 7, wherein the formulation is in the form selected from the group consisting of a tablet, pill, powder, sachet, elixir, suspension, emulsion, solution, syrup, aerosol, soft and hard gelatin capsule, sterile injectable solution, and sterile packaged powder.

10. The pharmaceutical formulation of claim 7, wherein the pharmaceutical formulation is preferably administered to mammals at a dose of 0.001-10 mg/kg.

11. The pharmaceutical formulation of claim 7, further comprising another antiviral agent.

12. The pharmaceutical formulation of claim 11, wherein the antiviral agent comprises one or more selected from the group consisting of interferon, anti-HBV monoclonal antibodies, anti-HBV polyclonal antibodies, nucleoside analogues, DNA polymerase inhibitors, and siRNA preparations.

13. The pharmaceutical formulation of claim 7, wherein the YMDD mutation is a M552V or M552I mutation.

14. The pharmaceutical formulation of claim 7, wherein the virus is mutant hepatitis B virus (HBV) resistant to lamivudine, adefovir dipivoxil, or HBIG (hepatitis B immunoglobulin).

15. The pharmaceutical formulation of claim 7, wherein the antibody is contained at a concentration of 0.1-50 mg/ml.

* * * * *

UNITED STATES PATENT AND TRADEMARK OFFICE
CERTIFICATE OF CORRECTION

PATENT NO. : 9,683,029 B2  Page 1 of 1
APPLICATION NO. : 14/412138
DATED : June 20, 2017
INVENTOR(S) : Se-Ho Kim et al.

It is certified that error appears in the above-identified patent and that said Letters Patent is hereby corrected as shown below:

In the Specification

Column 3, Line 18: "BEST NODE FOR CARRYING" should be --BEST MODE FOR CARRYING--.

Signed and Sealed this
First Day of August, 2017

Joseph Matal
*Performing the Functions and Duties of the*
*Under Secretary of Commerce for Intellectual Property and*
*Director of the United States Patent and Trademark Office*

SEQUENCE LISTING

<160> NUMBER OF SEQ ID NOS: 13

<210> SEQ ID NO 1
<211> LENGTH: 129
<212> TYPE: PRT
<213> ORGANISM: Artificial
<220> FEATURE:
<223> OTHER INFORMATION: variable region of human antibody H chain

<400> SEQUENCE: 1

Gln Val Lys Leu Leu Glu Ser Gly Gly Gly Leu Val Lys Pro Gly Gly

```
                1               5                   10                  15
            Ser Leu Arg Leu Ser Cys Ser Ala Ser Gly Phe Ser Leu Thr Lys Tyr
                        20                  25                  30

Lys Met Thr Trp Val Arg Gln Ala Pro Gly Lys Gly Leu Glu Trp Val
                        35                  40                  45

Ser Ser Ile Ser Ser Thr Ser Arg Asp Ile Asp Tyr Ala Asp Ser Val
                    50                  55                  60

Lys Gly Arg Phe Thr Ile Ser Arg Asp Asn Ala Lys Asn Ser Leu Phe
            65                  70                  75                  80

Leu Gln Met Ser Ser Leu Arg Val Asp Asp Thr Ala Val Tyr Tyr Cys
                            85                  90                  95

Thr Arg Asp Gly Trp Leu Trp Gly Trp Asp Val Arg Ser Asn Tyr Tyr
                        100                 105                 110

Tyr Asn Ala Leu Asp Val Trp Gly Gln Gly Thr Thr Val Thr Val Ser
                        115                 120                 125

Ser

<210> SEQ ID NO 2
<211> LENGTH: 129
<212> TYPE: PRT
<213> ORGANISM: Artificial
<220> FEATURE:
<223> OTHER INFORMATION: variable region of human antibody H chain

<400> SEQUENCE: 2

Glu Val Gln Leu Val Glu Ser Gly Gly Gly Leu Val Lys Pro Gly Gly
            1               5                   10                  15

Ser Leu Arg Leu Ser Cys Ser Ala Ser Gly Phe Ser Leu Thr Lys Tyr
                        20                  25                  30

Lys Met Thr Trp Val Arg Gln Ala Pro Gly Lys Gly Leu Glu Trp Val
                        35                  40                  45

Ser Ser Ile Ser Ser Thr Ser Arg Asp Ile Asp Tyr Ala Asp Ser Val
                    50                  55                  60

Lys Gly Arg Phe Thr Ile Ser Arg Asp Asn Ala Lys Asn Ser Leu Phe
            65                  70                  75                  80

Leu Gln Met Ser Ser Leu Arg Val Asp Asp Thr Ala Val Tyr Tyr Cys
                            85                  90                  95

Thr Arg Asp Gly Trp Leu Trp Gly Trp Asp Val Arg Ser Asn Tyr Tyr
                        100                 105                 110

Tyr Asn Ala Leu Asp Val Trp Gly Gln Gly Thr Thr Val Thr Val Ser
                        115                 120                 125

Ser

<210> SEQ ID NO 3
<211> LENGTH: 117
<212> TYPE: PRT
<213> ORGANISM: Artificial
<220> FEATURE:
<223> OTHER INFORMATION: variable region of human antibody H chain

<400> SEQUENCE: 3

Gln Val Gln Leu Val Gln Ser Gly Gly Glu Val Lys Lys Pro Gly Ala
            1               5                   10                  15

Leu Met Lys Val Ser Cys Lys Ala Ser Gly Tyr Ile Phe Thr Ser Tyr
                        20                  25                  30

Gly Ile Ser Trp Val Arg Gln Ala Pro Gly Gln Gly Leu Glu Trp Ile
                        35                  40                  45
```

```
Gly Trp Ile Asn Thr Tyr Ser Gly His Thr Asn Tyr Ala Arg Lys Phe
        50                  55                  60

Arg Gly Arg Val Thr Met Thr Trp Asp Thr Ser Thr Ser Thr Ala Tyr
65                  70                  75                  80

Met Glu Leu Ser Ser Leu Arg Ser Asp Asp Thr Ala Val Tyr Tyr Cys
                85                  90                  95

Ala Arg Val Pro Thr Trp Gly Ile Asp Tyr Trp Gly Gln Gly Thr Leu
                100                 105                 110

Val Thr Val Ser Ser
        115

<210> SEQ ID NO 4
<211> LENGTH: 117
<212> TYPE: PRT
<213> ORGANISM: Artificial
<220> FEATURE:
<223> OTHER INFORMATION: variable region of human antibody H chain

<400> SEQUENCE: 4

Gln Val Gln Leu Val Gln Ser Gly Gly Glu Val Lys Lys Pro Gly Ala
1               5                   10                  15

Leu Met Lys Val Ser Cys Lys Ala Ser Gly Tyr Ile Phe Thr Ser Tyr
                20                  25                  30

Gly Ile Ser Trp Val Arg Gln Ala Pro Gly Gln Gly Leu Glu Trp Ile
            35                  40                  45

Gly Trp Ile Asn Thr Tyr Ser Gly His Thr Asn Tyr Ala Arg Lys Phe
        50                  55                  60

Arg Gly Arg Val Thr Met Thr Trp Asp Thr Ser Thr Ser Thr Ala Tyr
65                  70                  75                  80

Met Glu Leu Ser Ser Leu Arg Ser Asp Asp Thr Ala Val Tyr Tyr Cys
                85                  90                  95

Ala Arg Val Pro Thr Trp Gly Ile Asp Tyr Trp Gly Gln Gly Thr Leu
                100                 105                 110

Val Thr Val Ser Ser
        115

<210> SEQ ID NO 5
<211> LENGTH: 117
<212> TYPE: PRT
<213> ORGANISM: Artificial
<220> FEATURE:
<223> OTHER INFORMATION: variable region of human antibody H chain

<400> SEQUENCE: 5

Gln Val Gln Leu Val Gln Ser Gly Gly Glu Val Lys Lys Pro Gly Ala
1               5                   10                  15

Leu Met Lys Val Ser Cys Lys Ala Ser Gly Tyr Ile Phe Thr Ser Tyr
                20                  25                  30

Gly Ile Ser Trp Val Arg Gln Ala Pro Gly Gln Gly Leu Glu Trp Ile
            35                  40                  45

Gly Trp Ile Asn Thr Tyr Ser Gly His Thr Asn Tyr Ala Arg Lys Phe
        50                  55                  60

Arg Gly Arg Val Thr Met Thr Trp Asp Thr Ser Thr Ser Thr Ala Tyr
65                  70                  75                  80

Met Glu Leu Ser Ser Leu Arg Ser Asp Asp Thr Ala Val Tyr Tyr Cys
                85                  90                  95

Ala Arg Val Pro Thr Trp Gly Ile Asp Tyr Trp Gly Gln Gly Thr Leu
```

Val Thr Val Ser Ser
        115

<210> SEQ ID NO 6
<211> LENGTH: 108
<212> TYPE: PRT
<213> ORGANISM: Artificial
<220> FEATURE:
<223> OTHER INFORMATION: variable region of human antibody L chain

<400> SEQUENCE: 6

Glu Leu Val Met Thr Gln Ser Pro Ser Ser Leu Ser Ala Ser Val Gly
1               5                   10                  15

Asp Arg Val Thr Ile Thr Cys Arg Ala Ser Gln Gly Ile Tyr Asn Ser
            20                  25                  30

Ile Ala Trp Tyr Gln Gln Lys Pro Gly Lys Ala Pro Lys Leu Leu Leu
        35                  40                  45

Tyr Ser Thr Ser Thr Leu Leu Ser Gly Val Pro Ser Arg Phe Ser Gly
    50                  55                  60

Ser Gly Ser Gly Thr Asp Tyr Thr Leu Thr Ile Thr Asn Leu Gln Pro
65                  70                  75                  80

Glu Asp Phe Ala Thr Tyr Tyr Cys Gln Gln Tyr Phe Val Thr Pro Glu
                85                  90                  95

Thr Phe Gly Gln Gly Thr Lys Val Glu Ile Lys Arg
            100                 105

<210> SEQ ID NO 7
<211> LENGTH: 108
<212> TYPE: PRT
<213> ORGANISM: Artificial
<220> FEATURE:
<223> OTHER INFORMATION: variable region of human antibody L chain

<400> SEQUENCE: 7

Asp Ile Val Val Thr Gln Ser Pro Ser Ser Leu Ser Ala Ser Val Gly
1               5                   10                  15

Asp Arg Val Thr Ile Thr Cys Arg Ala Ser Gln Gly Ile Tyr Asn Ser
            20                  25                  30

Ile Ala Trp Tyr Gln Gln Lys Pro Gly Lys Ala Pro Lys Leu Leu Leu
        35                  40                  45

Tyr Ser Thr Ser Thr Leu Leu Ser Gly Val Pro Ser Arg Phe Ser Gly
    50                  55                  60

Ser Gly Ser Gly Thr Asp Tyr Thr Leu Thr Ile Thr Asn Leu Gln Pro
65                  70                  75                  80

Glu Asp Phe Ala Thr Tyr Tyr Cys Gln Gln Tyr Phe Val Thr Pro Glu
                85                  90                  95

Thr Phe Gly Gln Gly Thr Lys Leu Glu Ile Lys Arg
            100                 105

<210> SEQ ID NO 8
<211> LENGTH: 107
<212> TYPE: PRT
<213> ORGANISM: Artificial
<220> FEATURE:
<223> OTHER INFORMATION: variable region of human antibody L chain

<400> SEQUENCE: 8

Gln Ala Gly Leu Thr Gln Pro Pro Ser Val Ser Val Ala Pro Gly Lys
1               5                   10                  15

```
Thr Ala Arg Ile Thr Cys Gly Gly Asp Asn Ile Gly Arg Lys Ser Val
            20                  25                  30

His Trp Tyr Gln Gln Lys Thr Gly Gln Ala Pro Val Leu Val Val Tyr
            35                  40                  45

Glu Asp Asn Lys Arg Pro Ser Gly Ile Pro Glu Arg Phe Ser Gly Ser
50                  55                  60

Asn Ser Gly Asn Thr Ala Thr Leu Thr Ile Ser Gly Thr Gln Ala Met
65                  70                  75                  80

Asp Glu Ala Asp Tyr Tyr Cys Gln Ala Trp Asp Ser Ser Thr Val Val
                85                  90                  95

Phe Gly Gly Gly Thr Lys Leu Thr Val Leu Gly
                100                 105

<210> SEQ ID NO 9
<211> LENGTH: 108
<212> TYPE: PRT
<213> ORGANISM: Artificial
<220> FEATURE:
<223> OTHER INFORMATION: variable region of human antibody L chain

<400> SEQUENCE: 9

Glu Ile Val Leu Thr Gln Ser Pro Pro Ser Leu Ser Ala Ser Val Gly
1               5                   10                  15

Asp Arg Val Thr Ile Thr Cys Gln Ala Ser Gln Asp Ile Asn Asn Asn
            20                  25                  30

Val Asn Trp Phe Gln Gln Glu Pro Gly Lys Ala Pro Arg Leu Leu Ile
            35                  40                  45

Tyr Asp Ala Ser Asn Leu Gln Thr Gly Val Pro Ser Arg Phe Ser Gly
        50                  55                  60

Ser Gly Ser Gly Thr Glu Phe Thr Leu Thr Ile Ser Ser Leu Gln Pro
65                  70                  75                  80

Glu Asp Phe Ala Thr Tyr Tyr Cys Gln Gln Thr Ser Val Tyr Pro Leu
                85                  90                  95

Thr Phe Gly Gly Gly Thr Lys Val Asp Ile Lys Arg
                100                 105

<210> SEQ ID NO 10
<211> LENGTH: 114
<212> TYPE: PRT
<213> ORGANISM: Artificial
<220> FEATURE:
<223> OTHER INFORMATION: variable region of human antibody L chain

<400> SEQUENCE: 10

Asp Ile Val Met Thr Gln Thr Pro Leu Ser Leu Pro Val Thr Pro Gly
1               5                   10                  15

Glu Pro Ala Ser Ile Ser Cys Arg Ser Ser Gln Ser Leu Leu His Ser
            20                  25                  30

Asn Gly Tyr Asn Tyr Leu Asp Trp Tyr Leu Gln Lys Pro Gly Gln Ser
            35                  40                  45

Pro Gln Leu Leu Ile Tyr Leu Gly Ser Lys Arg Ala Ser Gly Val Pro
        50                  55                  60

Asp Arg Phe Ser Gly Ser Gly Ser Gly Thr Asp Phe Thr Leu Gln Ile
65                  70                  75                  80

Ser Arg Val Glu Ala Glu Asp Val Gly Val Tyr Tyr Cys Met Gln Ser
                85                  90                  95

Thr Gln Phe Pro Pro Tyr Thr Phe Gly Gln Gly Thr Lys Leu Glu Ile
```

Lys Arg

<210> SEQ ID NO 11
<211> LENGTH: 25
<212> TYPE: DNA
<213> ORGANISM: Artificial
<220> FEATURE:
<223> OTHER INFORMATION: primer M3

<400> SEQUENCE: 11
ctgggaggag ttgggggagg agatt                                25

<210> SEQ ID NO 12
<211> LENGTH: 19
<212> TYPE: DNA
<213> ORGANISM: Artificial
<220> FEATURE:
<223> OTHER INFORMATION: primer POL8

<400> SEQUENCE: 12
aggatagaac ctagcaggc                                      19

<210> SEQ ID NO 13
<211> LENGTH: 832
<212> TYPE: PRT
<213> ORGANISM: Artificial Sequence
<220> FEATURE:
<223> OTHER INFORMATION: YMDD mutation of HBV DNA polymerase

<400> SEQUENCE: 13

```
Met Pro Leu Ser Tyr Gln His Phe Arg Lys Leu Leu Leu Leu Asp Asp
1               5                   10                  15

Glu Ala Gly Pro Leu Glu Glu Glu Leu Pro Arg Leu Ala Asp Glu Asp
            20                  25                  30

Leu Asn Arg Arg Val Ala Glu Asp Leu Asn Leu Gly Asn Leu Asn Val
        35                  40                  45

Ser Ile Pro Trp Thr His Lys Val Gly Asn Phe Thr Gly Leu Tyr Ser
50                  55                  60

Ser Thr Val Pro Val Phe Asn Pro His Trp Lys Thr Pro Ser Phe Pro
65                  70                  75                  80

Asn Ile His Leu His Gln Asp Ile Ile Lys Lys Cys Glu Gln Phe Val
                85                  90                  95

Gly Pro Leu Thr Val Asn Glu Lys Arg Arg Leu Gln Leu Ile Met Pro
            100                 105                 110

Ala Arg Phe Tyr Pro Asn Val Thr Lys Tyr Leu Pro Leu Asp Lys Gly
        115                 120                 125

Ile Lys Pro Tyr Tyr Pro Glu His Leu Val Asn His Tyr Phe Gln Thr
130                 135                 140

Arg His Tyr Leu His Thr Leu Trp Lys Ala Gly Ile Leu Tyr Lys Arg
145                 150                 155                 160

Glu Thr Thr Arg Ser Ala Ser Phe Cys Gly Ser Pro Tyr Ser Trp Glu
                165                 170                 175

Gln Glu Leu Gln His Gly Ala Glu Ser Phe His Gln Gln Ser Ser Gly
            180                 185                 190

Ile Leu Ser Arg Pro Pro Val Gly Ser Ser Leu Gln Ser Lys His Arg
        195                 200                 205

Lys Ser Arg Leu Gly Leu Gln Ser Gln Gln Gly His Leu Ala Arg Arg
210                 215                 220
```

```
Gln Gln Gly Arg Ser Trp Ser Ile Arg Ala Gly Ile His Pro Thr Ala
225                 230                 235                 240

Arg Arg Pro Phe Gly Val Glu Pro Ser Gly Ser Gly His Asn Thr Asn
            245                 250                 255

Leu Ala Ser Lys Ser Ala Ser Cys Ile Tyr Gln Ser Pro Val Arg Lys
        260                 265                 270

Ala Ala Tyr Pro Ala Val Ser Thr Phe Glu Lys His Ser Ser Ser Gly
    275                 280                 285

His Ala Val Glu Leu His Asn Phe Pro Pro Asn Ser Ala Arg Ser Gln
290                 295                 300

Gly Glu Arg Pro Val Phe Pro Cys Trp Trp Leu Gln Phe Arg Asn Ser
305                 310                 315                 320

Lys Pro Cys Ser Asp Tyr Cys Leu Ser His Ile Val Asn Leu Leu Glu
            325                 330                 335

Asp Trp Gly Pro Cys Thr Glu His Gly Glu His His Ile Arg Ile Pro
        340                 345                 350

Arg Thr Pro Ala Arg Val Thr Gly Gly Val Phe Leu Val Asp Lys Asn
    355                 360                 365

Pro His Asn Thr Ala Glu Ser Arg Leu Val Val Asp Phe Ser Gln Phe
370                 375                 380

Ser Arg Gly Asn His Arg Val Ser Trp Pro Lys Phe Ala Val Pro Asn
385                 390                 395                 400

Leu Gln Ser Leu Thr Asn Leu Leu Ser Ser Asn Leu Ser Trp Leu Ser
            405                 410                 415

Leu Asp Val Ser Ala Ala Phe Tyr His Leu Pro Leu His Pro Ala Ser
        420                 425                 430

Met Pro His Leu Leu Val Gly Ser Thr Gly Leu Ser Arg Tyr Val Ala
    435                 440                 445

Arg Val Ser Ser Asn Ser Arg Ile Phe Asn His Gln Arg Gly Thr Met
450                 455                 460

Gln Asn Leu His Asp Tyr Cys Ser Arg Asn Leu Tyr Val Ser Leu Leu
465                 470                 475                 480

Leu Leu Tyr Gln Thr Phe Gly Arg Lys Leu His Leu Tyr Ser His Pro
            485                 490                 495

Ile Ile Leu Gly Phe Arg Lys Ile Pro Met Gly Val Gly Leu Ser Pro
        500                 505                 510

Phe Leu Leu Ala Gln Phe Thr Ser Ala Ile Cys Ser Val Val Arg Arg
    515                 520                 525

Ala Phe Pro His Cys Leu Ala Phe Ser Tyr Met Asp Asp Val Val Leu
530                 535                 540

Gly Ala Lys Ser Val Gln His Leu Glu Ser Leu Phe Thr Ala Val Thr
545                 550                 555                 560

Asn Phe Leu Leu Ser Leu Gly Ile His Leu Asn Pro Asn Lys Thr Lys
            565                 570                 575

Arg Trp Gly Tyr Ser Leu His Phe Met Gly Tyr Val Ile Gly Ser Tyr
        580                 585                 590

Gly Ser Leu Pro Gln Asp His Ile Ile Gln Lys Ile Lys Glu Cys Phe
    595                 600                 605

Arg Lys Leu Pro Ile Asn Arg Pro Ile Asp Trp Lys Val Cys Gln Arg
610                 615                 620

Ile Val Gly Leu Leu Gly Phe Ala Ala Pro Phe Thr Gln Cys Gly Tyr
625                 630                 635                 640
```

-continued

```
Pro Ala Leu Met Pro Leu Tyr Ala Cys Ile Gln Ser Lys Gln Ala Phe
            645             650             655

Thr Phe Ser Pro Thr Tyr Lys Ala Phe Leu Cys Lys Gln Tyr Leu Asn
            660             665             670

Leu Tyr Pro Val Ala Arg Gln Arg Pro Gly Leu Cys Gln Val Phe Ala
            675             680             685

Asp Ala Thr Pro Thr Gly Trp Gly Leu Val Met Gly His Gln Arg Met
    690             695             700

Arg Gly Thr Phe Leu Ala Pro Leu Pro Ile His Thr Ala Glu Leu Leu
705             710             715             720

Ala Ala Cys Phe Ala Arg Ser Arg Ser Gly Ala Asn Ile Leu Gly Thr
            725             730             735

Asp Asn Ser Val Val Leu Ser Arg Lys Tyr Thr Ser Phe Pro Trp Leu
            740             745             750

Leu Gly Cys Ala Ala Asn Trp Ile Leu Arg Gly Thr Ser Phe Val Tyr
            755             760             765

Val Pro Ser Ala Leu Asn Pro Ala Asp Asp Pro Ser Arg Gly Arg Leu
    770             775             780

Gly Ile Phe Arg Pro Leu Leu Arg Leu Pro Phe Arg Pro Thr Thr Gly
785             790             795             800

Arg Thr Ser Leu Tyr Ala Asp Ser Pro Ser Val Pro Ser His Leu Pro
            805             810             815

Val Arg Val His Phe Ala Ser Pro Leu His Val Ala Trp Arg Pro Pro
            820             825             830
```